(12) United States Patent
Heckmeier et al.

(10) Patent No.: US 6,521,303 B2
(45) Date of Patent: Feb. 18, 2003

(54) LIQUID-CRYSTALLINE MEDIUM

(75) Inventors: Michael Heckmeier, Bensheim (DE);
Peer Kirsch, Darmstadt (DE); Brigitte Schuler, Haibach (DE); Achim Götz, Hähnlein (DE)

(73) Assignee: Merck Patent Fesellschaft mit, Darmstadt (DE)

( * ) Notice: Subject to any disclaimer, the term of this patent is extended or adjusted under 35 U.S.C. 154(b) by 142 days.

(21) Appl. No.: 09/732,887

(22) Filed: Dec. 11, 2000

(65) Prior Publication Data

US 2002/0025390 A1 Feb. 28, 2002

(30) Foreign Application Priority Data

Dec. 11, 1999 (DE) .......................... 199 59 797

(51) Int. Cl.[7] .................. C09K 19/30; C09K 19/12; C09K 19/20
(52) U.S. Cl. ............. 428/1.1; 252/299.63; 252/299.66; 252/299.67
(58) Field of Search ............ 252/299.01, 299.67, 252/299.63, 299.66; 428/1.1

(56) References Cited

FOREIGN PATENT DOCUMENTS

DE    19906254    *  9/1999

OTHER PUBLICATIONS

Caplus 1991: 112292.*

* cited by examiner

Primary Examiner—Shean C. Wu
(74) Attorney, Agent, or Firm—Millen, White, Zelano & Branigan, P.C.

(57) ABSTRACT

The invention relates to a liquid-crystalline medium based on a mixture of polar compounds having positive dielectric anisotropy, characterized in that it comprises one or more compounds of the general formula I

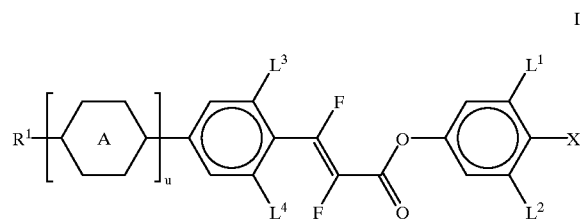

in which $R^1$,

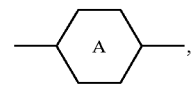

$L^1$, $L^2$, $L^3$, $L^4$, X and u are as defined in claim 1.

18 Claims, No Drawings

LIQUID-CRYSTALLINE MEDIUM

The present invention relates to a liquid-crystalline medium, and to the use thereof for electro-optical purposes and displays containing this medium.

Liquid crystals are used, in particular, as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN (twisted nematic) cells, STN (supertwisted nematic) cells, SBE (superbirefringence effect) cells and OMI (optical mode interference) cells. The most common display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have relatively low viscosity and give short addressing times, low threshold voltages and high contrast in the cells.

Furthermore, they should have a suitable mesophase, for example a nematic or cholesteric mesophase for the above-mentioned cells, at conventional operating temperatures, i.e. in the broadest possible range above and below room temperature. Since liquid crystals are generally used in the form of mixtures of a plurality of components, it is important that the components are readily miscible with one another. Further properties, such as the electrical conductivity, the dielectric anisotropy and the optical anisotropy, must satisfy different requirements depending on the cell type and area of application. For example, materials for cells having a twisted nematic structure should have positive dielectric anisotropy and low electrical conductivity.

For example, media of large positive dielectric anisotropy, broad nematic phases, relatively low birefringence, very high resistivity, good UV and temperature stability and low vapour pressure are desired for matrix liquid-crystal displays having integrated nonlinear elements for switching individual pixels (MLC displays).

Matrix liquid-crystal displays of this type are known. Examples of nonlinear elements which can be used for individual switching of individual pixels are active elements (i.e. transistors). This is then referred to as an "active matrix", and a differentiation can be made between two types:
1. MOS (metal oxide semiconductor) or other diodes on silicon wafers as substrate.
2. Thin-film transistors (TFTs) on a glass plate as substrate.

Use of monocrystalline silicon as the substrate material limits the display size, since even modular assembly of the various part-displays results in problems at the joints.

In the case of the more promising type 2, which is preferred, the electro-optical effect used is usually the TN effect. A differentiation is made between two technologies: TFTs comprising compound semiconductors, such as, for example, CdSe, or TFTs based on polycrystalline or amorphous silicon.

The TFT matrix is applied to the inside of one glass plate of the display, whilst the other glass plate carries the transparent counterelectrode on the inside. Compared with the size of the pixel electrode, the TFT is very small and has virtually no adverse effect on the image. This technology can also be extended to fully colour-compatible image displays, where a mosaic of red, green and blue filters is arranged in such a way that each filter element is located opposite a switchable pixel.

The TFT displays usually operate as TN cells with crossed polarizers in transmission and are illuminated from the back.

The term MLC displays here covers any matrix display containing integrated nonlinear elements, i.e., in addition to the active matrix, also displays containing passive elements, such as varistors or diodes (MIM=metal-insulator-metal).

MLC displays of this type are particularly suitable for TV applications (for example pocket TV sets) or for high-information displays for computer applications (laptops) and in automobile or aircraft construction. In addition to problems with respect to the angle dependence of the contrast and the response times, problems arise in MLC displays owing to inadequate resistivity of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display drops, and the problem of after-image elimination can occur. Since the resistivity of the liquid-crystal mixture generally drops over the life of an MLC display owing to interaction with the internal surfaces of the display, a high (initial) resistance is very important in order to obtain acceptable service lives. In particular in the case of low-voltage mixtures, it was hitherto not possible to achieve very high resistivities. It is furthermore important that the resistivity increases as little as possible with increasing temperature and after heating and/or exposure to UV radiation. Also particularly disadvantageous are the low-temperature properties of the mixtures from the prior art. It is required that crystallization and/or smectic phases do not occur, even at low temperatures, and that the temperature dependence of the viscosity is as low as possible. MLC displays of the prior art thus do not satisfy current requirements.

There thus continues to be a great demand for MLC displays having very high resistivity at the same time as a broad operating temperature range, short response times, even at low temperatures, and low threshold voltage which do not have these disadvantages or only do so to a reduced extent.

In the case of TN (Schadt-Helfrich) cells, media are desired which facilitate the following advantages in the cells:
broadened nematic phase range (in particular down to low temperatures),
switchability at extremely low temperatures (outdoor use, automobiles, avionics),
increased stability on exposure to UV radiation (longer life).

The media available from the prior art do not enable these advantages to be achieved while simultaneously retaining the other parameters.

In the case of supertwisted cells (STN), media are desired which enable greater multiplexibility and/or lower threshold voltages and/or broader nematic phase ranges (in particular at low temperatures). To this end, a further extension of the parameter latitude available (clearing point, smectic-nematic transition or melting point, viscosity, dielectric quantities, elastic quantities) is urgently desired.

The invention has an object of providing media, in particular for MLC, TN or STN displays of this type, and also in-plane switching (IPS) displays, which do not have the abovementioned disadvantages, or only do so to a reduced extent, and preferably at the same time have very high resistivities and low threshold voltages. In particular it is possible, using the compounds of the formula I, to prepare low $V_{th}$ mixtures having a very good $V_{th}/\gamma_1$ ratio.

Upon further study of the specification and appended claims, further objects and advantages of this invention will become apparent to those skilled in the art.

It has now been found that objects such as these can be achieved when novel media are used in displays.

The invention thus includes a liquid-crystalline medium based on a mixture of polar compounds having positive dielectric anisotropy, characterized in that it comprises one or more compounds of the general formula I,

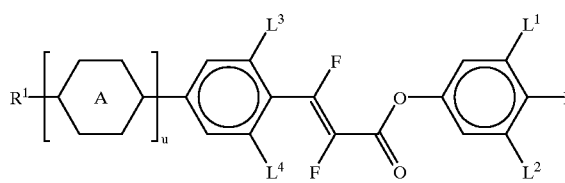

I in which
R is an alkyl radical having 1 to 12 carbon atoms which is unsubstituted, monosubstituted by CN or $CF_3$ or at least monosubstituted by halogen, it also being possible for one or more $CH_2$ groups in these radicals to be replaced, in each case independently of one another, by —O—, —S—,

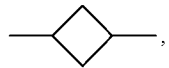

—CH=CH—, —C≡C—, —CO—, —CO—O—, —O—CO— or —O—CO—O— in such a way that O atoms are not linked directly to one another,

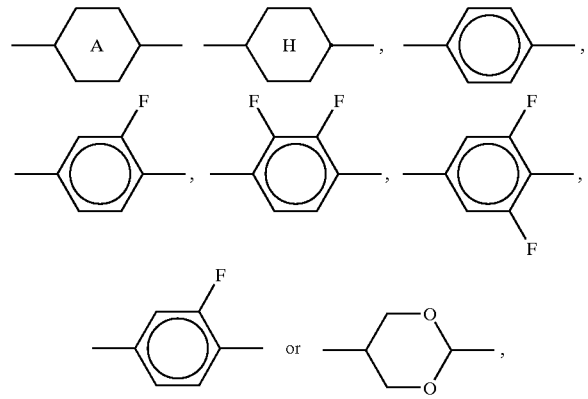

$L_{1-4}$ are, in each case independently of one another, H or F,
X is F, Cl, CN, OCN, NCS, SCN, halogenated alkyl radical, halogenated alkenyl radical, halogenated alkoxy radical or halogenated alkenyloxy radical having up to 6 carbon atoms, and
u is 0 or 1.

The compounds of the formula I have a broad range of applications. Depending on the choice of substituents, these compounds can serve as base materials from which liquid-crystalline media are predominantly composed; however, compounds of the formula I can also be added to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colourless and form liquid-crystalline mesophases in a temperature range which is favourably located for electro-optical use. They are stable chemically, thermally and to light.

If $R^1$ is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, methoxy, octoxy, nonoxy, decoxy or undecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkyl radical in which one $CH_2$ group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one $CH_2$ group has been replaced by —O— and one has been replaced by —CO—, these are preferably adjacent. These thus contain one acyloxy group —CO—O— or one oxycarbonyl group —O—CO—. These are preferably straight-chain and have 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxy-ethyl, 2-butyryloxyethyl, 3-acetoxypropyl, 3-pro-pionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl) ethyl, 3-(methoxycarbonyl)propyl, 3-(ethoxycarbonyl)propyl or 4-(methoxycarbonyl)butyl.

If $R^1$ is an alkyl radical in which one $CH_2$ group has been replaced by unsubstituted or substituted —CH=CH— and an adjacent $CH_2$ group has been replaced by CO or CO—O or O—CO, this can be straight-chain or branched. It is preferably straight-chain and has 4 to 12 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl.

If $R^1$ is an alkyl or alkenyl radical which is monosubstituted by CN or $CF_3$, this radical is preferably straight-chain. The substitution by CN or $CF_3$ is in any desired position.

If $R^1$ is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but preferably in the ω-position.

Compounds of the formula I which contain wing groups $R^1$ which are suitable for polyaddition reactions are suitable for the preparation of liquid-crystalline polyaddition products.

Compounds of the formula I containing branched wing groups $R^1$ may occasionally be of importance due to better solubility in the customary liquid-crystalline base materials, but in particular as chiral dopes if they are optically active. Smectic compounds of this type are suitable as components for ferroelectric materials.

Compounds of the formula I having $S_A$ phases are suitable, for example, for thermally addressed displays.

Branched groups of this type generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If $R^1$ is an alkyl radical in which two or more $CH_2$ groups have been replaced by —O— and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)-propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)-octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl and 5,5-bis(ethoxycarbonyl)-hexyl.

The compounds of the formula I are prepared by methods known per se, as described in the literature (for example in the standard works, such as Houben-Weyl, Methoden der Organischen Chemie, Georg-Thieme-Verlag, Stuttgart) or in DE 199 06 254 A1, to be precise under reaction conditions which are known and suitable for said reactions. Use can also be made here of variants which are known per se, but which are not mentioned here in greater detail.

The invention also relates to electro-optical displays (in particular STN or MLC displays having two plane-parallel outer plates which, together with a frame, form a cell, integrated nonlinear elements for switching individual pixels on the outer plates, and a nematic liquid-crystal mixture of positive dielectric anisotropy and high resistivity located in the cell) which contain media of this type, and to the use of these media for electro-optical purposes. The mixtures according to the invention are likewise suitable for IPS applications (In Plane Switching).

The liquid-crystal mixtures according to the invention facilitate a significant broadening of the parameter latitude available.

The achievable combinations of clearing point, rotation viscosity $\gamma_1$ and dielectric anisotropy are far superior to previous materials from the prior art.

The requirement for a high clearing point, a nematic phase at low temperature and a high $\Delta\epsilon$ was previously only achievable to an unsatisfactory extent. Although systems such as, for example, MLC-6424 have similar properties to the mixtures according to the invention, they have, however, clearly poorer values for the rotational viscosity $\gamma^1$.

Other mixture systems have comparable flow viscosities $v_{20}$ and values of $\Delta\epsilon$, but only have clearing points in the region of 60° C.

The liquid-crystal mixtures according to the invention make it possible to achieve clearing points of above 80°, preferably above 90°, particularly preferably above 100° C., and simultaneously dielectric anisotropy values $\Delta\epsilon \geq 6$, preferably $\geq 8$, and a high value for the resistivity while retaining the nematic phase down to −20° C. and preferably down to −30° C., particularly preferably down to −40° C., which allows excellent STN and MLC displays to be achieved. In particular, the mixtures are characterized by low operating voltages. The TN thresholds are preferably below 2.0 V, more preferably below 1.5 V, particularly preferably <1.3 V.

It goes without saying that a suitable choice of the components of the mixtures according to the invention also allows higher clearing points (for example above 110°) to be achieved at higher threshold voltages or lower clearing points to be achieved at lower threshold voltages while retaining the other advantageous properties. It is likewise possible to obtain mixtures of relatively high $\Delta\epsilon$ and thus relatively low thresholds if the viscosities are increased by a correspondingly small amount. The MLC displays according to the invention preferably operate in the first transmission minimum of Gooch and Tarry [C. H. Gooch and H. A. Tarry, Electron. Lett. 10, 2–4, 1974; C. H. Gooch and H. A. Tarry, Appl. Phys., Vol. 8, 1575–1584, 1975]; in this case, a lower dielectric anisotropy in the second minimum is sufficient in addition to particularly favourable electro-optical properties, such as, for example, high gradient of the characteristic line and low angle dependency of the contrast (German Patent 30 22 818) at the same threshold voltage as in an analogous display. This allows significantly higher resistivities to be achieved in the first minimum using the mixtures according to the invention than using mixtures containing cyano compounds. A person skilled in the art can use simple routine methods to produce the birefringence necessary for a prespecified layer thickness of the MLC display by a suitable choice of the individual components and their proportions by weight.

The flow viscosity $v_{20}$ at 20° C. is preferably <60 mm$^2$.s$^{-1}$, particularly preferably <50 mm$^2$.s$^{-1}$. The rotational viscosity $\gamma_1$ of the mixtures according to the invention at 20° C. is preferably <200 mPa.s, particularly preferably <180 mpa.s. The nematic phase range is preferably at least 90°, in particular at least 100°. This range preferably extends at least from −20° to +80°.

Measurements of the "capacity holding ratio" (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a considerably smaller decrease in the HR with increasing temperature than do analogous mixtures in which the compounds of the formula I are replaced by cyanophenylcyclohexanes of the formula

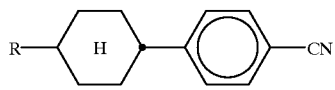

or esters of the formula

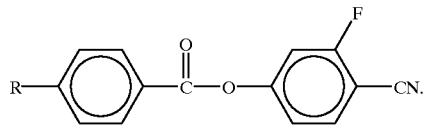

The UV stability of the mixtures according to the invention is also considerably better, i.e. they exhibit a significantly smaller decrease in the HR on exposure to UV radiation.

The media according to the invention are preferably based on a plurality (preferably two or more) of compounds of the formula I.

The individual compounds of the formulae I to XVIII and their sub-formulae which can be used in the media according to the invention are either known or can be prepared analogously to the known compounds.

Preferred embodiments are indicated below:

Medium comprises one or more compounds of the formulae I1 to I13:

I1

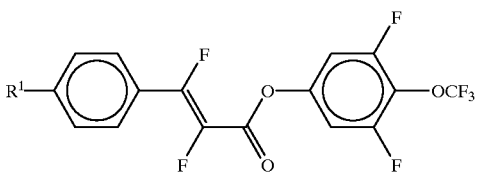

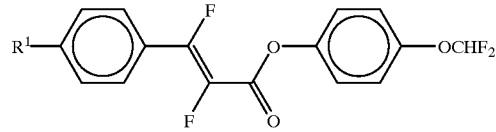

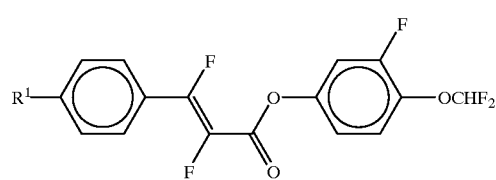

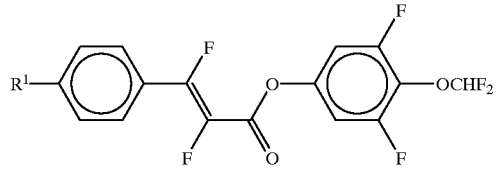

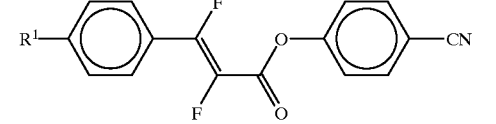

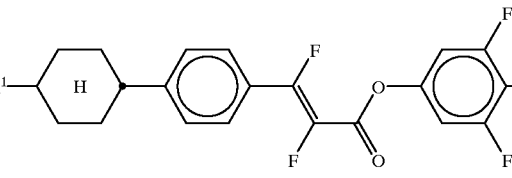

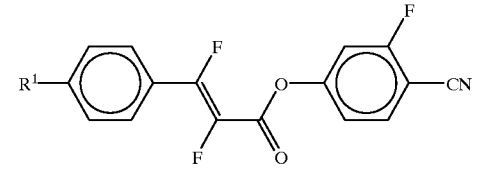

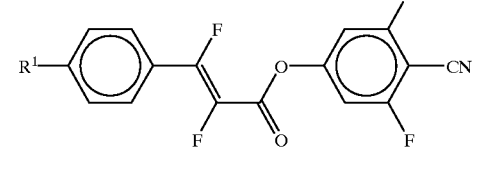

X is preferably F, Cl, CN, OCN, NCS, SCN, $CF_3$, $CF_2H$, $OCF_3$, $OCF_2H$, $OCFHCF_3$, $OCFHCH_2F$, $OCFHC_2HF$, $OCF_2CH_3$, $OCF_2CH_2F$, $OCF_2CHF_2$, $OCF_2CF_2CF_2H$, $OCF_2CF_2CH_2F$, $OCFHCF_2CF_3$, $OCFHCF_2CHF_2$, $OCFHCFHCF_3$, $OCH_2CF_2CF_3$, $QCF_2CF_2CF_3$, $OCF_2CFHCHF_2$, $OCF_2CH_2CHF_2$, $OCFHCF_2CHF_2$, $OCFHCFHCHF_2$, $OCFHCH_2CF_3$, $OCH_2CFHCF_3$, $OCH_2CF_2CHF_2$, $QCF_2CFHCH_3$, $OCF_2CH_2CHF_2$, OCFHCF₂CH₃, OCFHCFHCHF₂, OCFHCH₂CF₃, OCH₂CF₂CHF₂, OCH₂CFHCHF₂, OCF₂CH₂CH₃, OCFHCFHCH₃, OCFHCH₂CHF₂, OCH₂CF₂CH₃, OCH₂CFHCHF₂, OCH₂CH₂CHF₂, OCHCH₂CH₃, OCH₂CFHCH₃, OCH₂CH₂CHF₂, OCClFCF₃, OCClFCClF₂, OCClFCHF₂, OCFHCCl₂F, OCClFCHF₂, OCClFCClF₂, OCF₂CHCl₂, OCF₂CHCl₂, OCF₂CCl₂F, OCF₂CClFH, OCF₂CClF₂, OCF₂CF₂CClF₂, OCF₂CF₂CCl₂F, OCClFCF₂CF₃, OCClFCF₂CHF₂, OCClFCF₂CClF₂, OCClFCFHCF₃, OCClFCClFCF₃, OCCl₂CF₂CF₃, OCClHCF₂CF₃, OCClFCF₂CF₃, OCClFCClFCF₃, OCF₂CClFCHF₂, OCF₂CF₂CCl₂F, OCF₂CCl₂CHF₂, OCF₂CH₂CClF₂, OCClFCF₂CFH₂, OCFHCF₂CCl₂F, OCClFCFHCHF₂, OCClFCClFCF₂H, OCFHCFHCClF₂, OCClFCH₂CF₃, OCFHCCl₂CF₃, OCCl₂CFHCF₃, OCH₂CClFCF₃, OCCl₂CF₂CF₂H, OCH₂CF₂CClF₂, OCF₂CClFCH₃, OCF₂CFHCCl₂H, OCF₂CCl₂CFH₂, OCF₂CH₂CCl₂F, OCClFCF₂CH₃, OCFHCF₂CCl₂H, OCClFCClFCHF₂, OCFHCFHCCJ₂F, OCClFCH₂CF₃OCFHCCl₂CF₃, OCCl₂CF₂CFH₂, OCH₂CF₂CCl₂F, OCCl₂CFHCF₂H, OCClHCClFCF₂H, OCF₂CClHCClH₂, OCF₂CH₂CCl₂H, OCClFCFHCH₃, OCF₂CClFCCl₂H, OCClFCH₂CFH₂, OCFHCCl₂CFH₂, OCCl₂CF₂CH₃, OCH₂CF₂CClH₂, OCCl₂CFHCFH₂, OCH₂CClFCFCl₂, OCH₂CH₂CF₂H, OCClHCClHCF₂H, OCH₂CCl₂CF₂H, OCClFCH₂CH₃, OCFHCH₂CCl₂H, OCClHCFHCClH₂, OCH₂CFHCCl₂H, OCCl₂CH₂CF₂H, OCH₂CCl₂CF₂H, CH=CF₂, OCH=CFF₂, CF=CF₂, OCF=CF₂, CF=CHF, OCF=CHF, CH=CHF, OCH=CHF, CF₂CH₂CF₃, CF₂CHFCF₃ in particular F, Cl, CN, CF₃, CHF₂, OCF₃, OCHF₂, OCFHCF₃, OCFHCHF₂, OCFHGHF₂, OCF₂CH₃, OCF₂CHF₂, OCF₂CHF₂, OCF₂CF₂CHF₂, OCF₂CF₂CHF₂, OCFHCF₂CF₃, OCFHCF₂CHF₂, OCF₂CF₂CF₃, OCF₂CF₂CClF₂, OCClFCF₂CF₃ or CH=CHF₂.

Medium additionally comprises one or more compounds selected from the group consisting of the general formulae II to VIII:

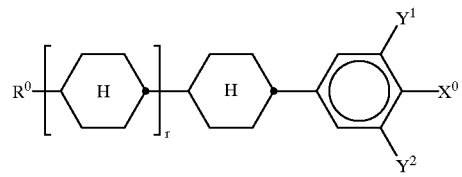

II

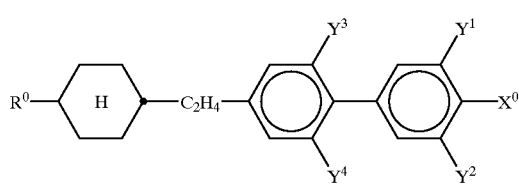

III

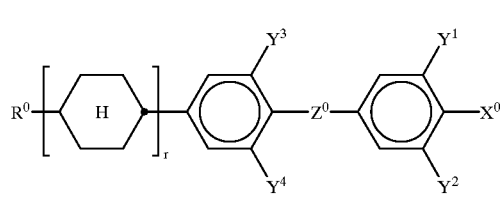

IV

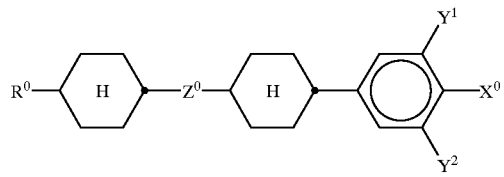

V

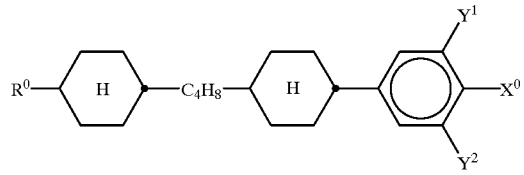

VI

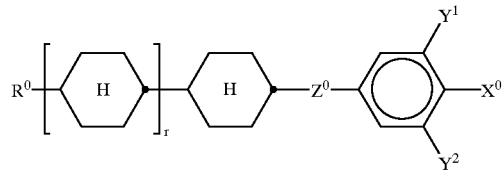

VII

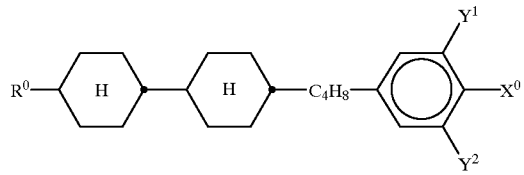

VIII in which the individual radicals have the following meanings:

$R^0$: n-alkyl, oxaalkyl, fluoroalkyl or alkenyl, in each case having up to 9 carbon atoms, $X^0$: F, Cl, halogenated alkyl, alkenyl or alkoxy having 1 to 6 carbon atoms, $Z^0$: —C₂H₄—, —CH₂O—, —COO—, —OCH₂—, —OCF₂—, —CF₂O— or —C₂F₄—, $Y^1$, $Y^2$, $Y^3$ and $Y^4$: in each case, independently of one another, H or F, r: 0 or 1.

The compound of the formula IV is preferably

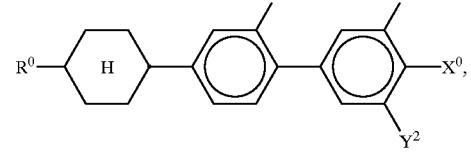

IVa

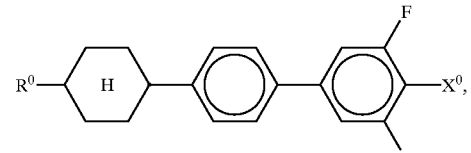

IVb

IVc

-continued

IVd
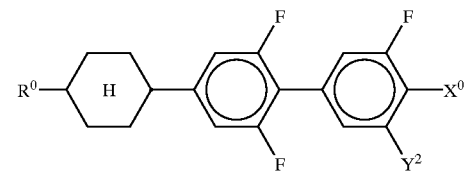

IVe
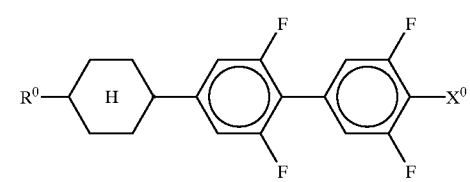

IVf
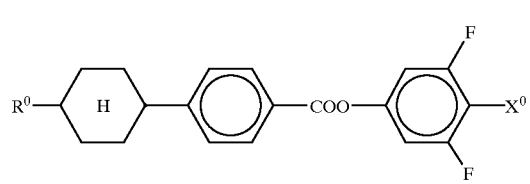

or

IVg
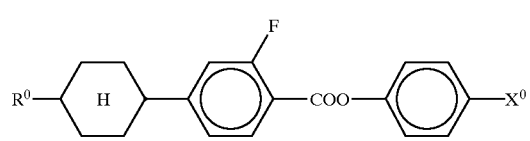

The medium additionally comprises one or more compounds selected from the group consisting of the general formulae IX to XVIII:

IX
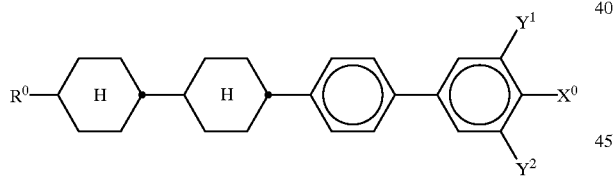

X

XI
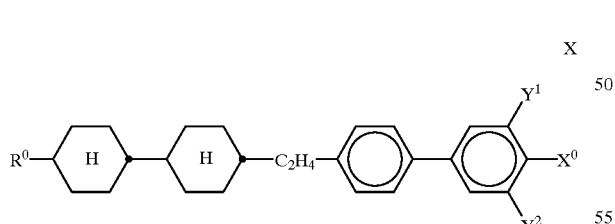

-continued

XII
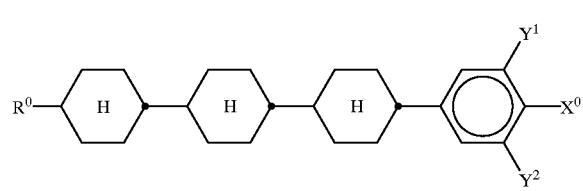

XIII

XIV

XV
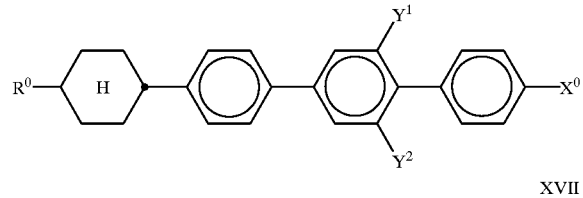

XVI

XVII
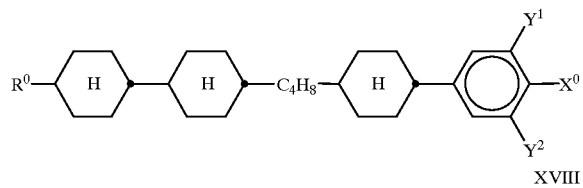

XVIII

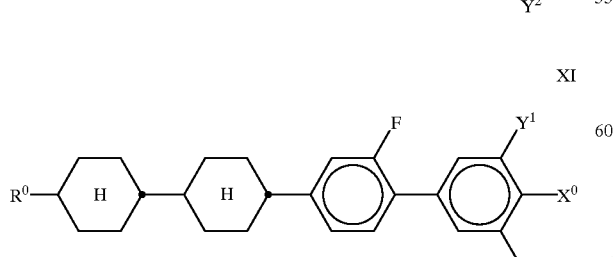

in which $R^0$, $X^0$, $Y^1$ and $Y^2$ are each, independently of one another, as defined above. $X^0$ is preferably F, Cl, $CF_3$, $OCF_3$, $OCHF_2$. $R^0$ is preferably alkyl, oxaalkyl, fluoroalkyl or alkenyl, in each case having up to 6 carbon atoms.

The medium additionally comprises one or more compounds having fused rings of the formulae A-1 to A-6:

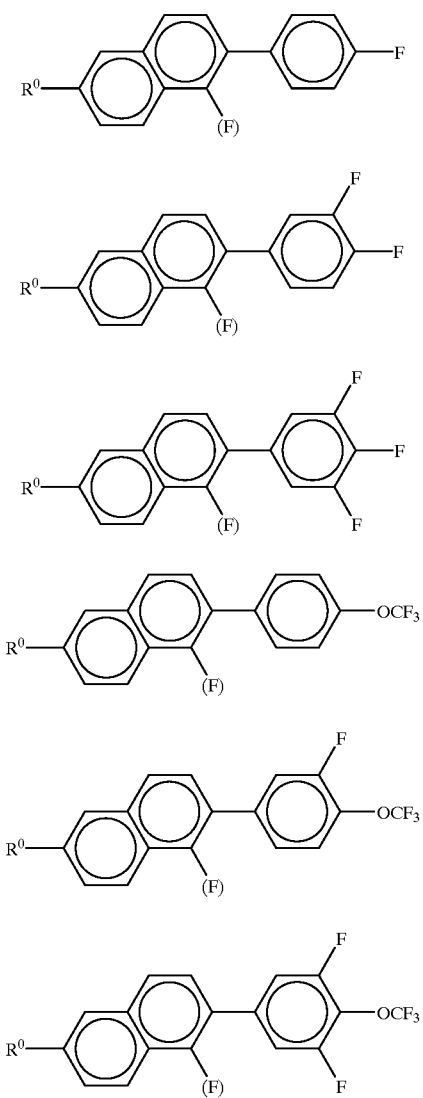

A-1
A-2
A-3
A-4
A-5
A-6

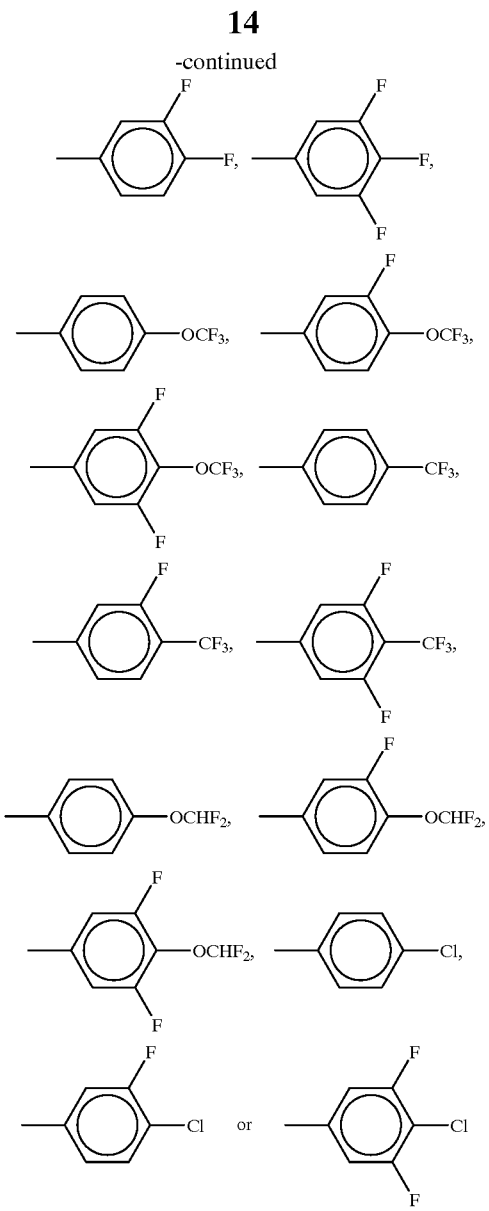

in which $R^0$ is as defined above.

The proportion of compounds of the formula A-1 to A-6 is 0–20% by weight, preferably 3–15% by weight, in particular 3–10% by weight.

The proportion of compounds of the formulae I to VIII together is at least 30% by weight, preferably at least 50% by weight, in the total mixture;

The proportion of compounds of the formula I is from 1 to 50% by weight, preferably 2–30% by weight and in particular 5–25% by weight, in the total mixture;

The proportion of compounds of the formulae II to VIII is from 20 to 80% by weight in the total mixture

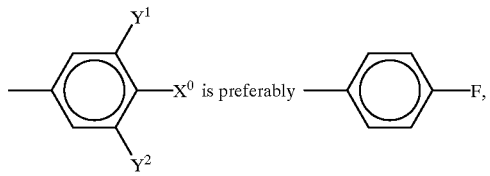

$X^0$ is preferably

The medium comprises one or more compounds of the formulae II, III, IV, V, VI, VII or VIII;

$R^0$ is straight-chain alkyl or alkenyl having 2 to 7 carbon atoms;

The medium essentially consists of compounds of the formulae I to VIII;

The medium preferably comprises one, two or three compounds of the formula I;

The medium comprises a mixture of compounds of the formula I in which $R^1$ is methyl, ethyl, n-$C_3H_7$, n-$C_4H_9$, n-$C_4H_9$, n-$C_5H_{11}$ or n-$C_6H_{11}$;

The medium comprises further compounds, preferably selected from the following group consisting of the general formulae XIX to XXII:

XIX

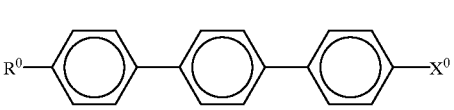

-continued

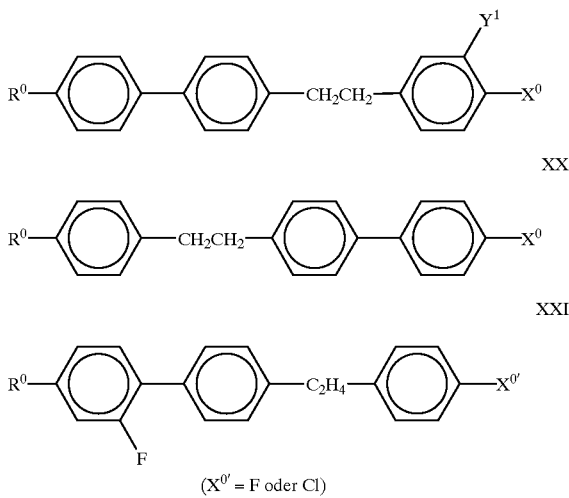

in which R⁰ and X⁰ are as defined above, and the 1,4-phenylene rings may be substituted by methyl, CN, chlorine or fluorine. The 1,4-phenylene rings are preferably monosubstituted or polysubstituted by fluorine atoms.

The medium preferably comprises carbocyclic dinuclear compounds of the formula XXIII

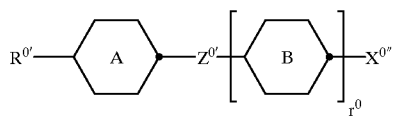

where

and

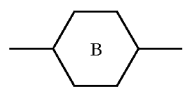

each independently of one another are

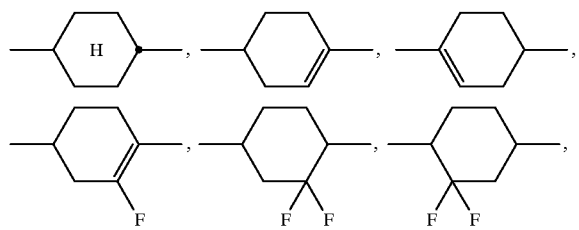

-continued

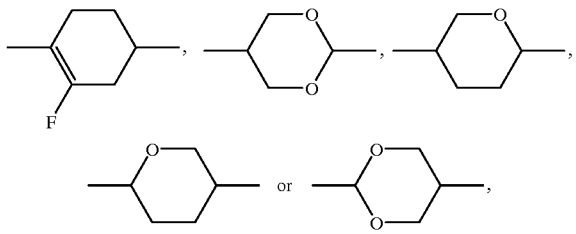

$Z^{0'}$ is a single bond, —$C_2H_4$—, —$C_4H_8$—, —COO—, —O—CO—, —$CF_2O$— or —$OCF_2$—, $r^0$ is 1 or 2, $R^{0'}$ is as defined for $R^0$ and $X^{0''}$ is $OCF_3$, F, Cl, $CF_3$, alkyl or alkoxy.

Preferred subformulae of the formula XXIII are

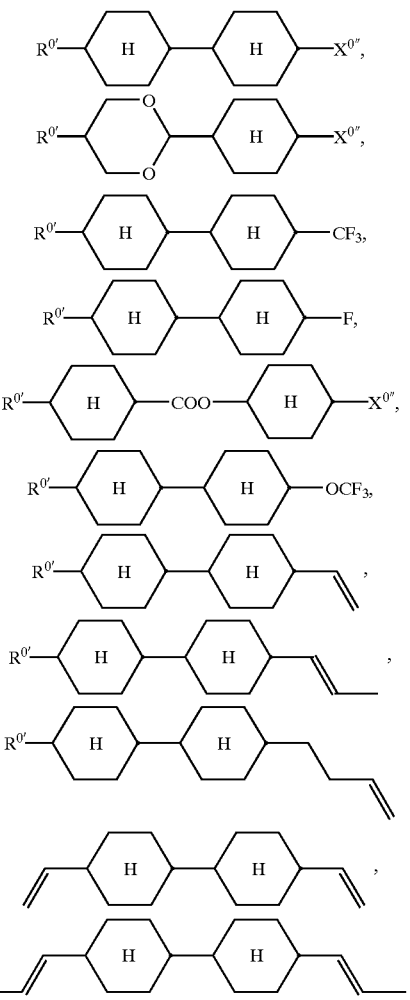

Very particularly preferred subformulae of the formula XXIII are

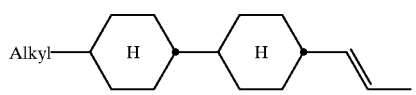

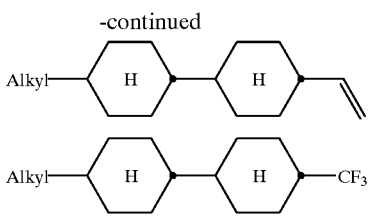

where

Alkyl is a straight-chain alkyl radical having 1–8 carbon atoms, especially having 2–5 carbon atoms.

The medium preferably comprises two or three compounds of the formulae XXIII.

The proportion of the compounds of the formula XXIII in the medium according to the invention is 5–40% by weight, especially 5–35% by weight.

The I: (II+III+IV+V+VI+VII+VIII) weight ratio is preferably from 1:10 to 10:1.

The medium essentially consists of compounds selected from the group consisting of the general formulae I to XVIII.

The term "alkyl" covers straight-chain and branched alkyl groups having 1–7 carbon atoms, in particular the straight-chain groups methyl, ethyl, propyl, butyl, pentyl, hexyl and heptyl. Groups having 2–5 carbon atoms are generally preferred.

The term "alkenyl" covers straight-chain and branched alkenyl groups having 2–7 carbon atoms, in particular the straight-chain groups. In particular, alkenyl groups are $C_2$–$C_7$ 1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups containing terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably 1 and m is preferably from 1 to 6.

It has been found that even a relatively small proportion of compounds of the formula I mixed with conventional liquid-crystal materials, but in particular with one or more compounds of the formula II, III, IV, V, VI, VII and/or VIII, results in a significant reduction in the threshold voltage and in low birefringence values, and at the same time broad nematic phases with low smectic-nematic transition temperatures are observed, thus improving the shelf life. Particular preference is given to mixtures which, in addition to one or more compounds of the formula I, comprise one or more compounds of the formula IV, in particular compounds of the formula IVa and/or IVd in which $X^0$ is F, $OCHF_2$ or $OCF_3$. The compounds of the formulae I to VIII are colourless, stable and readily miscible with one another and with other liquid-crystal materials. Moreover, the mixtures of the invention are also notable for very high curing points, the values for the rotational viscosity $\gamma_1$ being comparatively low.

Through a suitable choice of the meanings of $R^0$ and $X^0$, the addressing times, the threshold voltage, the gradient of the transmission characteristic lines, etc., can be modified as desired. For example, 1E-alkenyl radicals, 3E-alkenyl radicals, 2E-alkenyloxy radicals and the like generally give shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals.

A —$CH_2CH_2$— group generally results in higher values of $k_{33}/k_{11}$ compared with a simple covalent bond. Higher values of $k_{33}/k_{11}$ facilitate, for example, flatter transmission characteristic lines in TN cells with a 90° twist (for achieving grey tones) and steeper transmission characteristic lines in STN, SBE and OMI cells (greater multiplexibility), and vice versa.

The optimum mixing ratio of the compounds of the formulae I and II+III+IV+V+VI+VII+VIII depends substantially on the desired properties, on the choice of the components of the formulae I, II, III, IV, V, VI, VII and/or VIII and on the choice of any other components which may be present. Suitable mixing ratios within the abovementioned range can easily be determined from case to case.

The total amount of compounds of the formulae I to XVIII in the mixtures according to the invention is not crucial. The mixtures may therefore contain one or more further components in order to optimize various properties. However, the effect observed on the addressing times and the threshold voltage is generally greater the higher the total concentration of compounds of the formulae I to XVIII.

In a particularly preferred embodiment, the media according to the invention comprise compounds of the formulae II to VIII (preferably II, III and/or IV, in particular IVa) in which $X^0$ is F, $OCF_3$, $OCHF_2$, $OCH=CF_2$, $OCF=CF_2$ or $OCF_2$—$CF_2H$. A favourable synergistic effect with the compounds of the formula I results in particularly advantageous properties. In particular, mixtures comprising compounds of the formula I and of the formula IVa are distinguished by their low threshold voltages.

The construction of the MLC display according to the invention from polarizers, electrode base plates and electrodes with surface treatment corresponds to the construction which is conventional for displays of this type. The term conventional construction here is broadly drawn and also covers all derivatives and modifications of the MLC display, in particular also matrix display elements based on poly-Si TFTs or MIMs.

An essential difference between the displays according to the invention and those customary hitherto based on the twisted nematic cell is, however, the choice of the liquid-crystal parameters in the liquid-crystal layer.

The liquid-crystal mixtures which can be used according to the invention are prepared in a manner which is conventional per se. In general, the desired amount of the components used in the lesser amount is dissolved in the components making up the principal constituent, expediently at elevated temperature. It is also possible to mix solutions of the components in an organic solvent, for example in acetone, chloroform or methanol, and, after thorough mixing, to remove the solvent again, for example by distillation.

The dielectrics may also contain other additives known to those skilled in the art and described in the literature. For example, 0–15% of pleochroic dyes or chiral dopes can be added.

C denotes a crystalline phase, S a smectic phase, $S_C$ a smectic C phase, N a nematic phase and I the isotropic phase.

$V_{10}$ denotes the voltage for 10% transmission (view angle perpendicular to the plate surface) $t_{on}$ denotes the switch-on time and $t_{off}$ the switch-off time at an operating voltage corresponding to 2.5 times the value of $V_{10}$. Δn denotes the optical anisotropy and $n_o$ the refractive index. Δε denotes the dielectric anisotropy (Δε=$ε_{81}$ −$ε_⊥$, where $ε_∥$ is the dielectric constant parallel to the longitudinal molecular axes and $ε_⊥$ is the dielectric constant perpendicular thereto). The electro-optical data were measured in a TN cell at the 1st minimum (i.e. at a d×Δn value of 0.5) at 20° C., unless expressly stated otherwise. The optical data were measured at 20° C., unless expressly stated otherwise.

In the present application and in the examples below, the structures of the liquid-crystal compounds are indicated by acronyms, with the transformation into chemical formulae taking place in accordance with Tables A and B below. All radicals $C_nH_{2n+1}$ and $C_mH_{2m+1}$ are straight-chain alkyl radicals containing n or m carbon atoms, respectively; n and m are preferably 0, 1, 2, 3, 4, 5, 6 or 7. The coding in Table B is self-evident. In Table A, only the acronym for the base structure is given. In individual cases, the acronym for the base structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| n$CF_3$ | $C_nH_{2n+1}$ | $CF_3$ | H | H |
| n$OCF_3$ | $C_nH_{2n+1}$ | $OCF_3$ | H | H |
| n$OCF_2$ | $C_nH_{2n+1}$ | $OCHF_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |
| n$OCCF_2$.F.F | $C_nH_{2n+1}$ | $OCH_2CF_2H$ | F | F |
| V-n | $CH_2$=CH | $C_nH_{2n+1}$ | H | H |

Preferred mixture components of the mixture concept according to the invention are shown in Tables A and B.

TABLE A

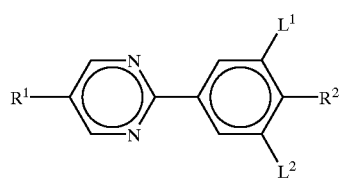

PYP

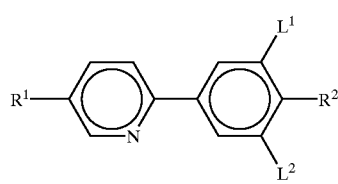

PYRP

TABLE A-continued

BCH

CBC

CCH

CCP

CPTP

CEPTP

ECCP

CECP

TABLE A-continued
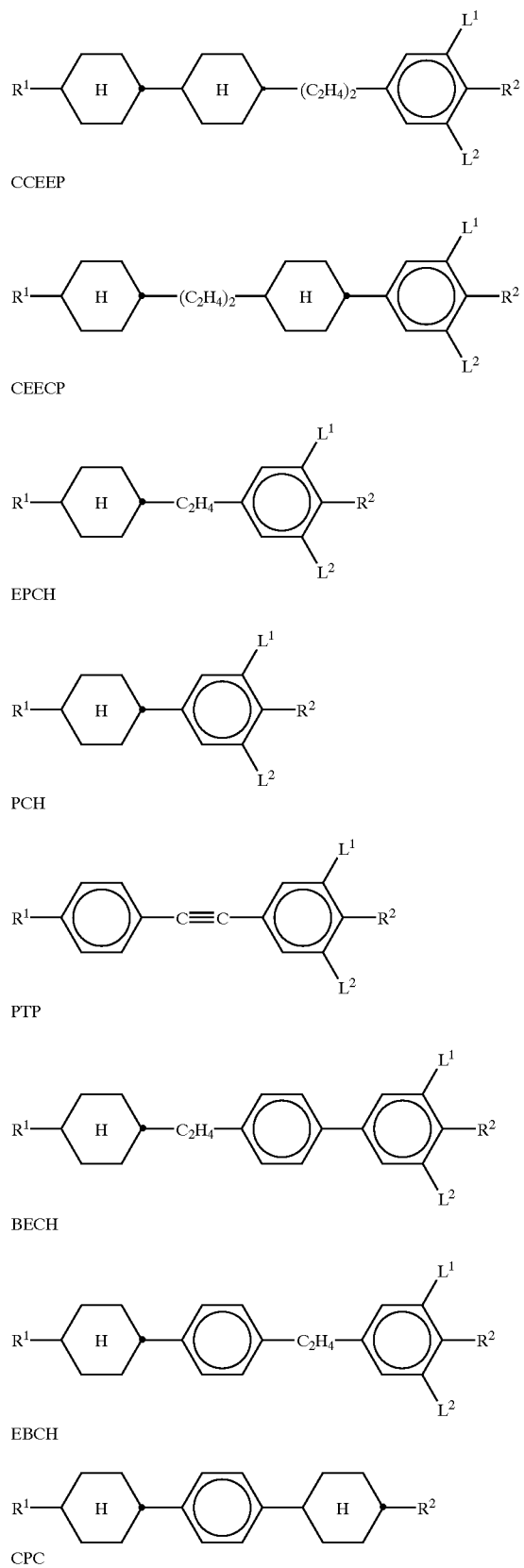
TABLE A-continued
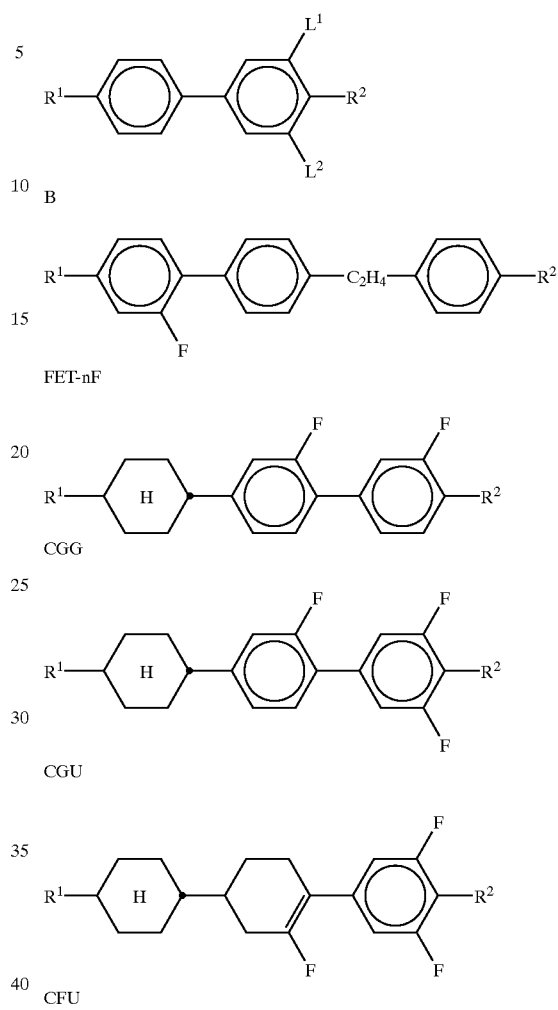
TABLE B
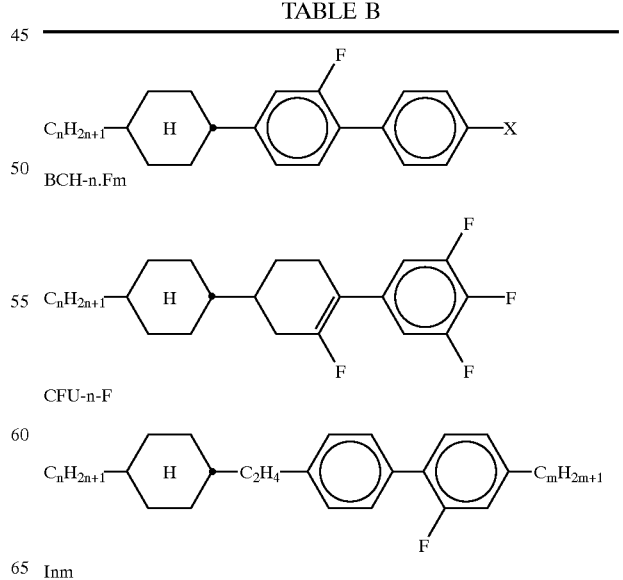

TABLE B-continued

CBC-nmF

PDX-n

CCZU-n-F

K3n

ECCP-nm

CCH-n1EM

T-nFm

CGU-n-F

CDU-n-X

CGG-n-F

CWC-n-m

CCH-nCF$_3$

CUP-nF.F

CC-n-V

CWCC-n-m

CQCU-n-F

CCG-n-OT

CCU-n-OT

CCQU-n-F

CCQG-n-OT

TABLE B-continued
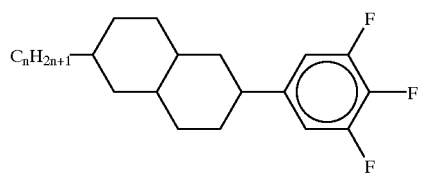
Dec-U-n-F
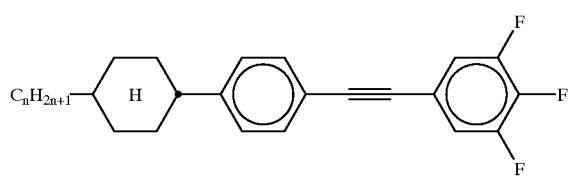
CPTU-n-F
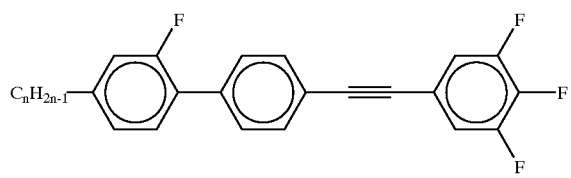
GPTU-n-F
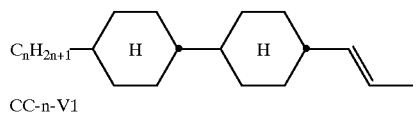
CC-n-V1
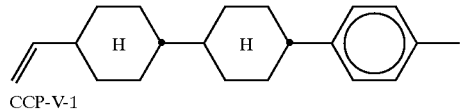
CCP-V-1
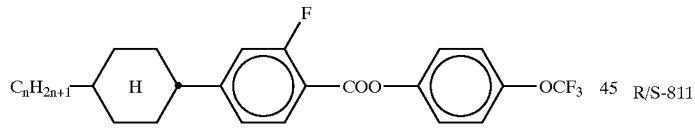
CGZP-n-OT
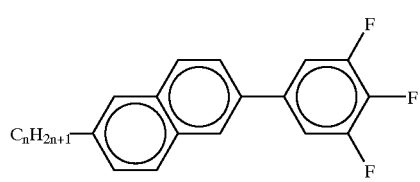
Nap-U-n-F
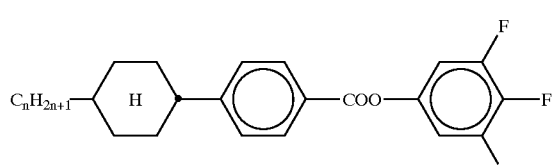
CPZU-n-F
TABLE B-continued
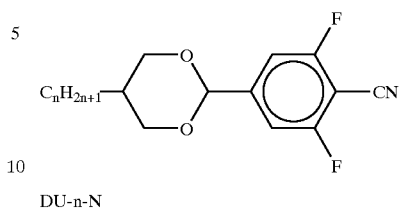
DU-n-N
TABLE C
Table C indicates possible dopants which are generally added to the mixtures according to the invention.
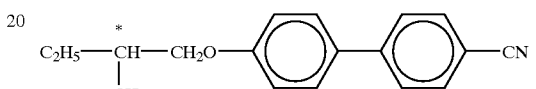
C 15
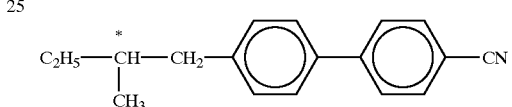
CB 15
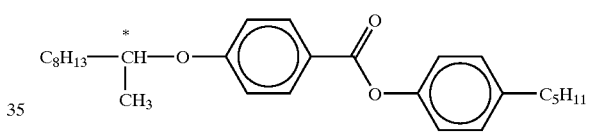
CM 21
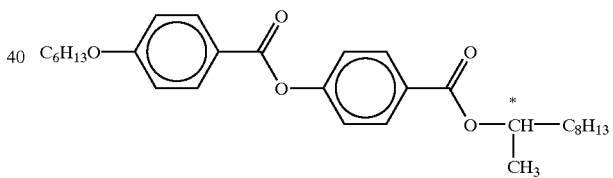
R/S-811
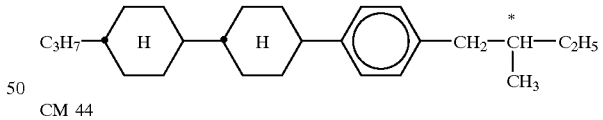
CM 44
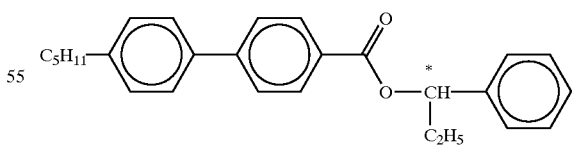
CM 45
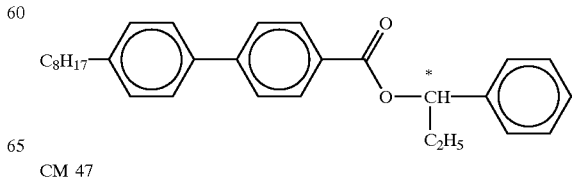
CM 47

TABLE C-continued

Table C indicates possible dopants which are generally added to the mixtures according to the invention.

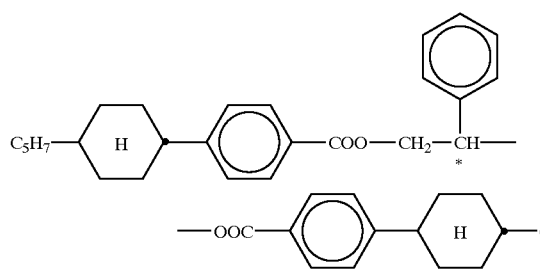

R/S-1011

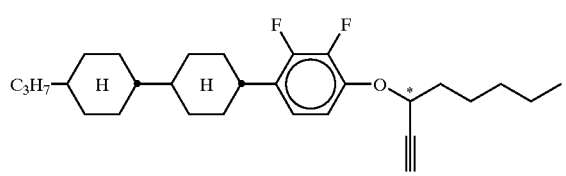

R/S-3011

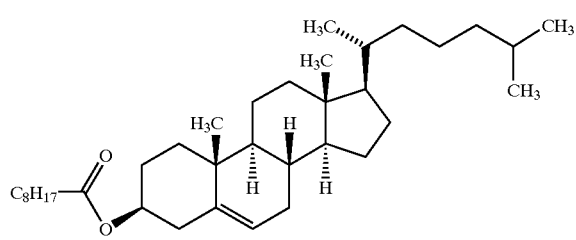

CN

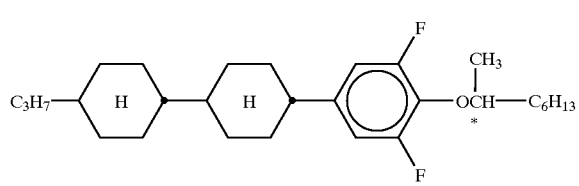

R/S-2011

Particularly preferred mixtures comprise, in addition to one or more compounds of the formula I, one, two, three, four, five or more compounds from Table B.

The entire disclosure of all applications, patents and publications, cited above and of corresponding application No. DE No. 19959797.9, filed December 11, 1999 is hereby incorporated by reference.

EXAMPLES

The examples below are intended to illustrate the invention without representing a limitation. Above and below, percentages are percent by weight. All temperatures are given in degrees Celsius. m.p. denotes melting point, c.p.= clearing point. Furthermore, C=crystalline state, N=nematic phase, S=smectic phase and I=isotropic phase. The data between these symbols represent the transition temperatures. An denotes the optical anisotropy (589 nm, 20° C.). The flow viscosity $v_{20}$ (mm²/sec) and the rotation viscosity $y_1$ (mPa·s) were in each case determined at 20° C.

Mixture Examples

| | | | |
|---|---|---|---|
| CC-3-V1 | 9.00% | Clearing point: | +72.5 |
| CC-5-V | 22.00% | Δn [589 nm, 20° C.]: | +0.0886 |
| CCP-2F.F.F | 9.00% | $\gamma_1$ [mPa · s, 20° C.]: | 81 |
| CCP-20CF$_3$ | 3.00% | $V_{10}$: | 1.34 V |
| CCP-30CF$_3$ | 3.00% | | |
| CGU-2-F | 10.00% | | |
| CGU-3-F | 7.00% | | |
| CCZU-2-F | 4.00% | | |
| CCZU-3-F | 15.00% | | |
| CGZP-2-OT | 5.00% | | |
| CCP-V-1 | 3.00% | | |
| A | 10.00% | | |

A =

H$_7$C$_3$—⬡—C(F)=C(F)—C(=O)—O—⬡—OCF$_3$

| | | | |
|---|---|---|---|
| BCH-3F.F | 10.77% | Clearing point [° C.]: | 91.5 |
| BCH-5F.F | 8.97% | Δn [589 nm, 20° C.]: | +0.1057 |
| ECCP-30CF$_3$ | 4.49% | Δε [1 kHz, 20° C.]: | +6.9 |
| ECCP-50CF$_3$ | 4.49% | | |
| CBC-33F | 1.79% | | |
| CBC-53F | 1.79% | | |
| CBC-55F | 1.79% | | |
| PCH-6F | 7.18% | | |
| PCH-7F | 5.38% | | |
| CCP-20CF$_3$ | 7.18% | | |
| CCP-30CF$_3$ | 10.77% | | |
| CCP-40CF$_3$ | 6.28% | | |
| CCP-50CF$_3$ | 9.87% | | |
| PCH-5F | 8.97% | | |
| A | 10.28% | | |

| | | | |
|---|---|---|---|
| BCH-3F.F | 10.86% | Clearing point [° C.]: | 91.5 |
| BCH-5F.F | 9.05% | $\gamma_1$ [mPa · s, 20° C.]: | 125 |
| ECCP-30CF$_3$ | 4.52% | | |
| ECCP-50CF$_3$ | 4.52% | | |
| CBC-33F | 1.81% | | |
| CBC-53F | 1.81% | | |
| CBC-55F | 1.81% | | |
| PCH-6F | 7.24% | | |
| PCH-7F | 5.43% | | |
| CCP-20CF$_3$ | 7.24% | | |
| CCP-30CF$_3$ | 10.86% | | |
| CCP-40CF$_3$ | 6.33% | | |
| CCP-50CF$_3$ | 9.95% | | |
| PCH-5F | 9.05% | | |
| A | 9.53% | | |

| | |
|---|---|
| CC-3-V1 | 9.00% |
| CC-3-V | 19.00% |
| CC-5-V | 2.00% |
| CCP-2F.F.F | 9.00% |
| CCP-20CF$_3$ | 3.00% |
| CCP-30CF$_3$ | 3.00% |
| CGU-2-F | 10.00% |
| CGU-3-F | 7.00% |
| CCZU-2-F | 4.00% |
| CCZU-3-F | 15.00% |
| CGZP-2-OT | 5.00% |

-continued

| | |
|---|---|
| CCP-V-1 | 4.00% |
| A | 10.00% |

| | | | |
|---|---|---|---|
| BCH-3F.F | 10.77% | Δn [589 nm, 20° C.]: | +0.1034 |
| BCH-5F.F | 8.98% | Δε [1 kHz, 20° C.]: | 7.6 |
| ECCP-30CF₃ | 4.49% | | |
| ECCP-50CF₃ | 4.49% | | |
| CBC-33F | 1.80% | | |
| CBC-53F | 1.80% | | |
| CBC-55F | 1.80% | | |
| PCH-6F | 7.18% | | |
| PCH-7F | 5.39% | | |
| CCP-20CF₃ | 7.18% | | |
| CCP-30CF₃ | 10.77% | | |
| CCP-40CF₃ | 6.28% | | |
| CCP-50CF₃ | 9.87% | | |
| PCH-5F | 8.98% | | |
| B | 10.23% | | |

B = 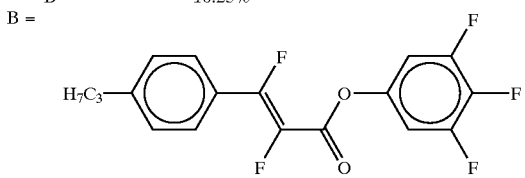

| | | | |
|---|---|---|---|
| BCH-3F.F | 10.80 | γ₁ [mPa · s 20° C.]: | 120 |
| BCH-3F.F | 9.00 | | |
| ECCP-30CF₃ | 4.50 | | |
| ECCP-50CF₃ | 4.50 | | |
| CBC-33F | 1.80 | | |
| CBC-53F | 1.80 | | |
| CBC-55F | 1.80 | | |
| PCH-6F | 7.20 | | |
| PCH-7F | 5.40 | | |
| CCP-20CF₃ | 7.20 | | |
| CCP-30CF₃ | 10.80 | | |
| CCP-40CF₃ | 6.30 | | |
| CCP-50CF₃ | 9.90 | | |
| PCH-5F | 9.00 | | |
| B | 10.00 | | |

| | |
|---|---|
| CC-3-V1 | 9.00% |
| CCH-35 | 5.00% |
| CCH-3CF₃ | 7.00% |
| CCP-2F.F.F | 11.00% |
| CCP-3F.F.F | 9.00% |
| CCP-20CF₃ | 7.00% |
| B | 11.00% |
| CCZU-2-F | 5.00% |
| CCZU-3-F | 15.00% |
| CCZU-5-F | 3.00% |
| CGZP-2-OT | 11.00% |
| CGZP-3-OT | 7.00% |

| | | | |
|---|---|---|---|
| CC-3-V1 | 10.00% | Clearing point [° C.]: | +70.0 |
| CC-3-V | 18.00% | Δn [589 nm, 20° C.]: | +0.0943 |
| CCH-35 | 3.00% | Δε [1 kHz, 20° C.]: | +12.9 |
| CCP-20CF₃ | 8.00% | γ₁ [mPa · s, 20° C.]: | 66 |
| CCP-30CF₃ | 7.00% | | |

-continued

| | |
|---|---|
| DU-3-N | 14.00% |
| ME2N.F | 3.00% |
| PDX-3 | 4.00% |
| CGZP-2-OT | 8.00% |
| BCH-32 | 5.00% |
| CCP-V-1 | 13.00% |
| C | 7.00% |

| | | | |
|---|---|---|---|
| CC-3-V1 | 9.00% | Clearing point [° C.]: | +70.5 |
| CC-3-V | 18.00% | Δn [589 nm, 20° C.]: | +0.0932 |
| CC-5-V | 3.00% | Δε [1 kHz, 20° C.]: | +12.0 |
| CCH-35 | 4.00% | | |
| CCP-20CF₃ | 8.00% | | |
| CCP-30CF₃ | 7.00% | | |
| DU-3-N | 11.00% | | |
| ME2N.F | 3.00% | | |
| PDX-3 | 4.00% | | |
| CGZP-2-OT | 8.00% | | |
| BCH-32 | 3.00% | | |
| CCP-V1 | 12.00% | | |
| C | 10.00% | | |

C =

$C_2H_5$—⌬—C(=CF)—C(F)=C(—O—⌬—$OCF_3$)—O (structural formula)

What is claimed is:

1. A liquid-crystalline medium based on a mixture of polar compounds having positive dielectric anisotropy, which comprises one or more compounds of the formula I, $$R^1—[A]_u—\text{(aryl with } L^3, L^4, F\text{)}—C(F)=C(F)—CO—O—\text{(aryl with } L^1, L^2\text{)}—X$$ (I)

in which $R^1$ is an alkyl radical having 1 to 12 carbon atoms which is unsubstituted, monosubstituted by CN or $CF_3$ or mono- to per halo- substituted by halogen, optionally one or more $CH_2$ groups in these radicals optionally being replaced, in each case independently of one another, by

◇ ,

—CH=CH—, —C≡C—, —CO—, —CO—O—, —O—CO— or —O—CO—O— in such a way that O atoms are not linked directly to one another,

⬡(A), ⬡(H)•, ⬯ ,

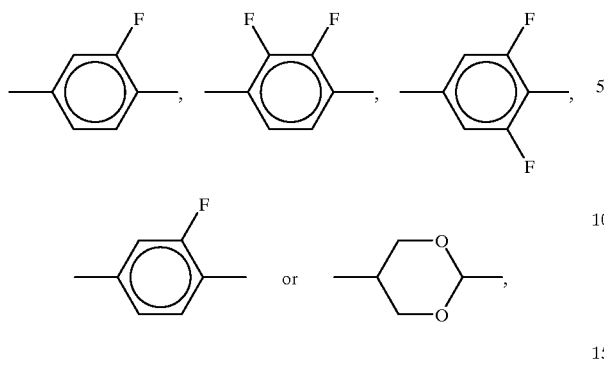

$L^{1-4}$ are, in each case independently of one another, H or F,

X is F, Cl, CN, OCN, NCS, SCN, halogenated alkyl radical, halogenated alkenyl radical, halogenated alkoxy radical or halogenated alkenyloxy radical having up to 6 carbon atoms, and u is 0 or 1, wherein said medium further comprises one or more compounds selected from the group consisting of the formula II, III, IV, V, VII, and VIII:

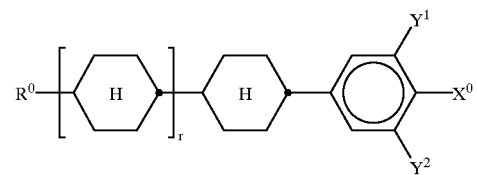

II

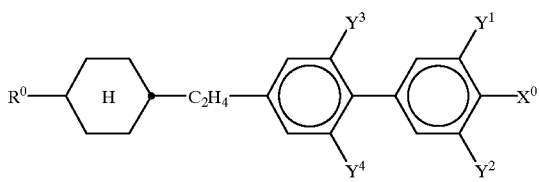

III

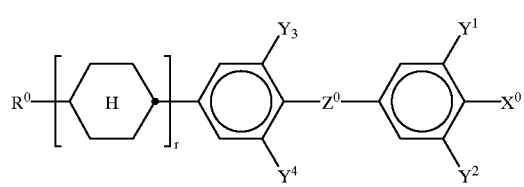

IV

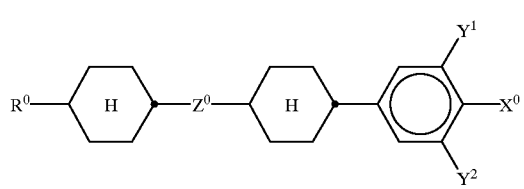

V

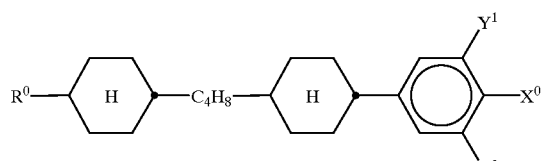

VI

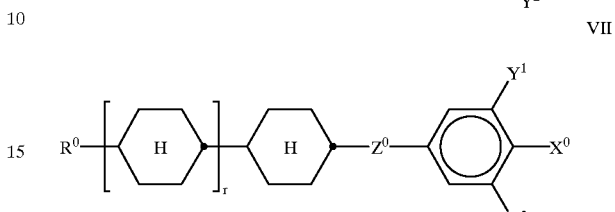

VII

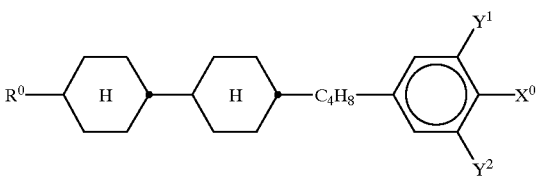

VIII in which the individual radicals have the following meanings:

$R^0$ n-alkyl, oxaalkyl, fluoroalkyl or alkenyl, in each case having up to 9 carbon atoms, $X^0$: F, Cl, halogenated alkyl, alkenyl or alkoxy having 1 to 6 carbon atoms, $Z^0$: —$C_2H_4$—, $CH_2O$—, —$OCH_2$—, —COO—, —$OCF_2$, —$CF_2O$— or —$C_2F_4$—, $Y^1$ and $Y^2$: in each case, independently of one another, H or F, r: 0 or 1.

2. The medium according to claim 1, wherein the proportion of compounds of the formulae I to VIII together is at least 30% by weight in the total mixture.

3. The medium according to claim 1, wherein the proportion of compounds of the formula I is from 1 to 50% by weight in the total mixture.

4. The medium according to claim 1, wherein the proportion of compounds of the formulae II to VIII is from 20 to 80% by weight in the total mixture.

5. The medium according to claim 1, comprising one or more compounds of the formula IVa and/or IVd

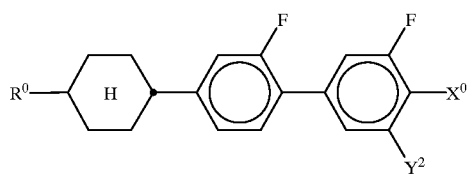

IVa

IVd

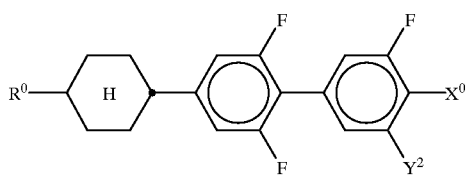

in which $R^0$, $X^0$ and $Y^2$ are

- $R^0$: n-alkyl, oxaalkyl, fluoroalkyl or alkenyl, in each case having up to 9 carbon atoms,
- $X^0$: F, Cl, halogenated alkyl, alkenyl or alkoxy having 1 to 6 carbon atoms,
- $Y^1$ and $Y^2$: in each case, independently of one another, H or F.

6. The medium according to claim 1, wherein $X^0$ is F, $OCHF_2$ or $OCF_3$, and $Y^2$ is H or F.

7. The medium according to claim 5, wherein $X^0$ is F, $OCHF_2$ or $OCF_3$, and $Y^2$ is H or F.

8. The medium according to claim 1, wherein $R^1$ in the compound of the formula I is straight-chain alkyl.

9. An electro-optical liquid-crystal display containing a liquid-crystalline medium according to claim 1.

10. The medium according to claim 1 which exhibits a clearing point above 80° C., a dielectric anisotropy value of 6 and maintains a nematic phase down to −20° C.

11. The medium according to claim 10 which exhibits a TN threshold below 2.0V.

12. The electro-optical liquid-crystal device according to claim 9, which is an IPS MLC, TN or STN display.

13. The liquid-crystalline medium according to claim 1, wherein the medium has a flow viscosity at 20° C. of less than 60 mm²·s⁻¹.

14. The liquid-crystalline medium according to claim 1, wherein the medium has a rotational viscosity at 20° C. of less than 200 mPa·s.

15. The liquid-crystalline medium according to claim 1, wherein the medium has a nematic phase range of −20° C. to +80° C.

16. A liquid-crystalline medium according to claim 3, wherein the medium contains 5 to 25% by weight of compounds of the formula I.

17. The liquid-crystalline medium according to claim 1, wherein at least one compound of the formula I is a compound of one of the following formulae:

I1

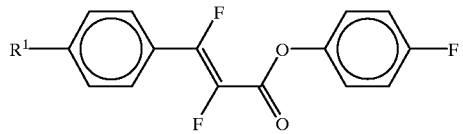

I2

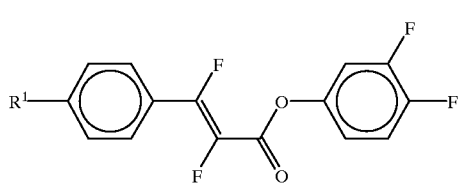

I3

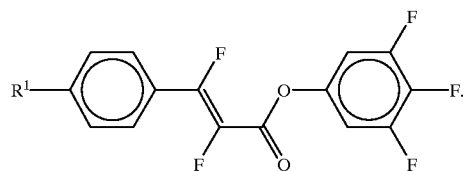

18. The liquid-crystalline medium according to claim 1, which comprises at least one compound of the formulae IVa to IVg:

IVa

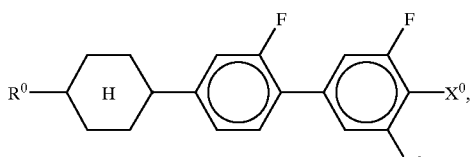

IVb

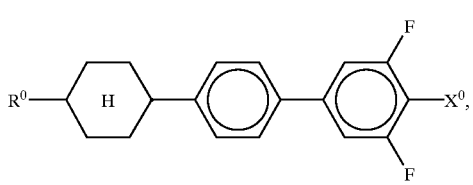

IVc

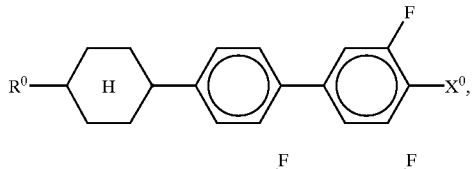

IVd

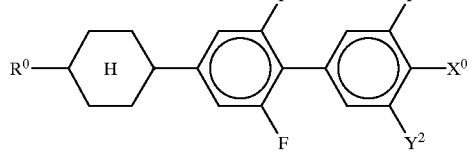

IVe

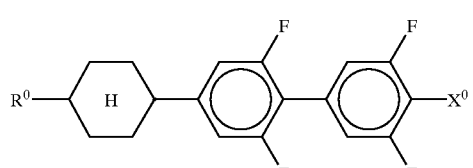

IVf

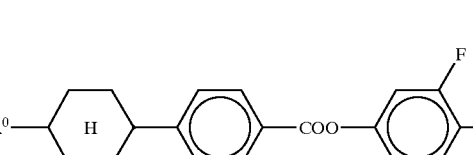

or

IVg

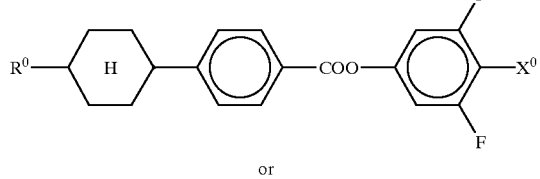

* * * * *

UNITED STATES PATENT AND TRADEMARK OFFICE
CERTIFICATE OF CORRECTION

PATENT NO. : 6,521,303 B2
DATED : February 18, 2003
INVENTOR(S) : Heckmeier et al.

It is certified that error appears in the above-identified patent and that said Letters Patent is hereby corrected as shown below:

Title page,
Item [73], Assignee, reads "Fesellschaft mit" should read -- Gesellshaft mit beschraenkter Haftung --

Column 30,
Line 53, reads "by" should read -- by -O-, -S-, --

Column 31,
Line 28, reads "of the" should read -- of those of the --

Column 32,
Line 33, reads "Ro n-alkyl," should read -- Ro: n-alkyl, --
Line 38, reads "CH2O-," should read -- $CH_2O$-, --

Signed and Sealed this

Eighth Day of June, 2004

JON W. DUDAS
*Acting Director of the United States Patent and Trademark Office*